United States Patent [19]

Miyashita et al.

[11] Patent Number: 5,556,998
[45] Date of Patent: Sep. 17, 1996

[54] TRANSITION METAL COMPLEX, PROCESS FOR THE PREPARATION OF THE SAME, AND ASYMMETRIC HYDROGENATION CATALYST COMPRISING THE SAME

[75] Inventors: Akira Miyashita, Saitama; Takeshi Chiba, Miyagi; Hiroyuki Nohira, Saitama; Hidemasa Takaya, Shiga, all of Japan

[73] Assignee: Takasago International Corporation, Tokyo, Japan

[21] Appl. No.: 402,692

[22] Filed: Mar. 13, 1995

[30] Foreign Application Priority Data

Sep. 14, 1994 [JP] Japan ................... 6-247032
Sep. 14, 1994 [JP] Japan ................... 6-247033

[51] Int. Cl.$^6$ ............... C07F 9/02; C07F 15/00; B01J 31/00
[52] U.S. Cl. .................. 556/21; 556/136; 502/162; 502/166; 502/213; 568/17
[58] Field of Search ............ 556/21, 136; 502/162, 502/166, 213

[56] References Cited

FOREIGN PATENT DOCUMENTS

| 0271311 | 6/1988 | European Pat. Off. . |
| 0271310 | 6/1988 | European Pat. Off. . |
| 0269395 | 6/1988 | European Pat. Off. . |

OTHER PUBLICATIONS

C. Landis, et al., "Asymmetric Hydrogenation of Methyl–(Z)–α–acetamidocinnamate Catalyzed by {1,2–Bis((phenyl–o–anisoyl)phosphino)ethane}rhodium(I): Kinetics, Mechanism, and Origin of Enantioselection", *J. Am. Chem. Soc.*, 1987, 109, 1746–1754.

B. McCulloch, et al., "Catalyst–Substrate Adducts in Asymmetric Catalytic Hydrogenation. Crystal and Molecular Structure of [((R,R)–1, 2–Bis{phenyl–o–anisoylphosphino}ethane) (methyl(Z)–β–propyl–α–acetamidoacrylate)]rhodium Tetrafluoroborate, [Rh(DIPAMP)(MPAA)]BF$_4$", *Organometallics* 1990, 9, 1392–1395.

M. Ashby, et al., "Crystal and Molecular Structure of an Asymmetric Hydrogenation Catalyst–Substrate Adduct, Δ–Bis(tiglato){(R)–2,2'–bis(diphenylphosphino)–1, 1'–binaphthyl}–ruthenium(II), [RuII(BINAP)(O$_2$CCMe=CHMe)$_2$]", *Organometallics* 1991, 10, 2011–2015.

*Primary Examiner*—Porfirio Nazario-Gonzales
*Attorney, Agent, or Firm*—Sughrue, Mion, Zinn, Macpeak & Seas

[57] ABSTRACT

The present invention provides a novel transition metal complex which catalyzes asymmetric hydrogenation reaction. The present invention also provides a process for the preparation of the foregoing novel complex. The present invention further provides an asymmetric hydrogenation catalyst comprising the foregoing novel complex. The novel transition metal complex is provided, represented by the following general formula (I):

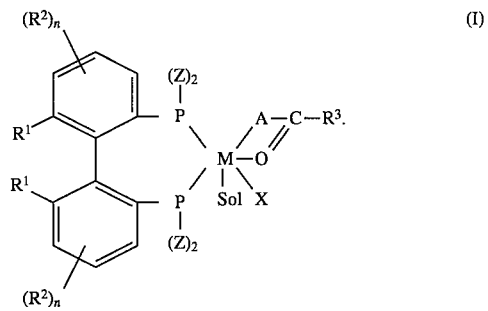

20 Claims, No Drawings

TRANSITION METAL COMPLEX, PROCESS FOR THE PREPARATION OF THE SAME, AND ASYMMETRIC HYDROGENATION CATALYST COMPRISING THE SAME

FIELD OF THE INVENTION

The present invention relates to a novel transition metal complex represented by the general formula (I) described below, a process for the preparation thereof, and an asymmetric hydrogenation catalyst comprising said complex.

BACKGROUND OF THE INVENTION

As intermediates in the synthesis of various useful compounds such as medicine and food flavorings, there have been known various optically active carboxylic acids. Representative examples of the methods for the preparation of these optically active carboxylic acids include a method which comprises the preparation from natural substances, a method which comprises the use of microorganism, and a method which comprises the use of an asymmetric hydrogenation catalyst. Among these methods, the method which comprises the use of an asymmetric hydrogenation catalyst attracts the most attention from the standpoint of availability of raw materials, reaction controllability and cost.

Beginning with the proposal for the process for the preparation of an asymmetrically-hydrogenated compound having a high optical purity by the selective use of a complex comprising as a ligand a rhodium atom and an optically active phosphine as an asymmetric hydrogenation catalyst, many studies of the use of a complex comprising a transition metal atom and optically active phosphine as an asymmetric hydrogenation catalyst have been reported.

For example, *J. Org. Chem.*, Vol. 52, No. 14, pp. 3174–3176 (1987) discloses a technique for the preparation of an optically active carboxylic acid which comprises the asymmetric hydrogenation of an unsaturated carboxylic acid in the presence of a 2,2'-bis(diphenylphosphino)-1,1'-binaphthyl-ruthenium complex catalyst (hereinafter referred to as "BINAP-Ru catalyst").

This method enables the preparation of a carboxylic acid having a high optical purity under milder conditions than the conventional methods and thus is useful. However, this method is disadvantageous in that the reaction must be effected at a hydrogen pressure of 1 to 100 atm. over tens of hours.

Further, *Tetrahedron Lett.*, vol. 34, pp. 2351–2354 (1993) discloses a technique for the asymmetric hydrogenation of tiglic acid in the presence of a catalyst comprising 2,2'-bis(dicyclohexylphosphino)-6,6'-dimethyl-1,1'-biphenyl (hereinafter referred to as "BICHEP") and p-cymene coordinated to a ruthenium atom.

Moreover, JP-A-63-310847 (The term "JP-A" as used herein means an "unexamined published Japanese patent application") discloses a technique for the preparation of an optically active alcohol which comprises the asymmetric hydrogenation of ketonic acids in the presence of BINAP-Ru catalyst.

This method enables the preparation of a carboxylic acid having a high optical purity under milder conditions than the conventional methods and thus is useful. However, this method is disadvantageous in that the reaction must be effected at a hydrogen pressure of 5 to 40 atm. over tens of hours.

On the other hand, a complex comprising ruthenium as a transition metal atom and an unsaturated acid as a ligand is disclosed in *J. Am. Chem. Soc.*, Vol. 113, No. 2, pp. 589–594 (1991). However, this reference discloses no idea of the use of such a complex as a catalyst for an asymmetric hydrogenation reaction. Further, this reference merely discloses that such a complex comprises two unsaturated acid molecules or one unsaturated acid molecule and one saturated acid molecule coordinated to ruthenium atom.

SUMMARY OF THE INVENTION

It is therefore an object of the present invention to provide a novel transition metal complex which catalyzes an asymmetric hydrogenation reaction.

It is another object of the present invention to provide a process for the preparation of the foregoing novel complex.

It is a further object of the present invention to provide an asymmetric hydrogenation catalyst comprising the foregoing novel complex.

These and other objects of the present invention will become more apparent from the following detailed description and examples.

The present inventors have made extensive studies of the mechanism of the asymmetric hydrogenation reaction of unsaturated acids or ketones to develop a useful asymmetric hydrogenation technique. Among the studies, it was found that a transition metal complex having a transition metal-unsaturated acid or ketone coordinated complex is isolated, and the transition metal complex thus isolated can act as a catalyst for an asymmetric hydrogenation reaction.

DETAILED DESCRIPTION OF THE INVENTION

The present invention will be further described hereinafter.

The complex of the present invention is a compound represented by the following general formula (I):

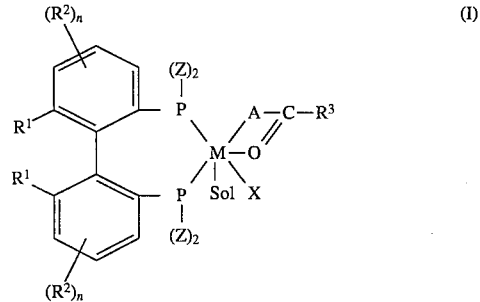

In the general formula (I), $R^1$ and $R^2$ each represents a halogen atom, a $C_{1-3}$ alkyl group such as methyl, ethyl and propyl, or a $C_{1-3}$ alkyl group substituted with a halogen atom. Preferably $R^1$ and $R^2$ each is a methyl group.

The suffix n represents 0 or an integer of from 1 to 3.

$R^1$ and $R^2$ are advantageously bonded to the position adjacent to carbon atom bonded to benzene ring.

Z represents a cyclohexyl group, a phenyl group, or a substituted phenyl group, wherein said substituted group is a $C_{1-4}$ alkyl group, a $C_{1-4}$ alkoxy group or a halogen atom. Particularly preferred among these groups are

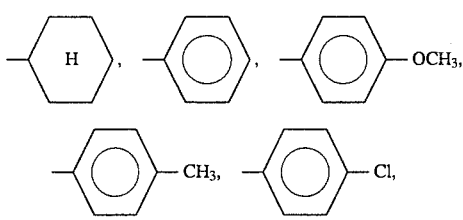

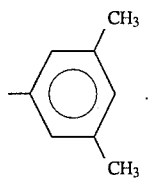

X represents a chlorine atom, a bromine atom, or an iodine atom.

M represents a ruthenium atom, a rhodium atom, an iridium atom, a palladium atom, or a platinum atom.

Sol represents a solvent. The term "solvent" as used herein means a solvent which is used in the preparation of the foregoing complex. The solvent is preferably one or more selected from the group consisting of aromatic hydrocarbons such as benzene and toluene, aprotic solvents such as tetrahydrofuran, ethyl acetate, acetone, dimethylformamide, dimethylacetamide and dimethyl sulfoxide, halogenated hydrocarbons such as methylene chloride and chloroform, and protonic solvents such as methanol, ethanol and isopropanol. Most preferred among these solvents are chloroform and methanol.

A represents —O— or —O=C(R$^4$)—, wherein R$^4$ is selected from the group consisting of

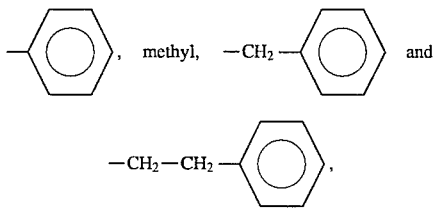

wherein the phenyl nucleus may be substituted with a C$_{1-4}$ alkyl group.

When A is —O—, R$^3$ represents —C(R$^7$)=C(R$^5$)R$^6$ and when A is —O=C(R$^4$)—, R$^3$ represents —NH-tert-butyl,

or OCH$_3$, wherein R$^5$, R$^6$ and R$^7$ each represents a hydrogen atom, a C$_{1-7}$ alkyl or alkenyl group which may be substituted, or a C$_{6-18}$ aryl or naphthyl group which may be substituted, with the proviso that R$^5$, R$^6$ and R$^7$ are not hydrogen atoms at the same time, that when R$^5$ and R$^6$ are hydrogen atoms at the same time, R$^7$ is not a methyl group, and that when R$^7$ is a hydrogen atom, R$^5$ and R$^6$ are different groups other than a hydrogen atom.

Preferred examples of R$^5$, R$^6$ and R$^7$ include hydrogen atom, methyl, ethyl, propyl, pentenyl, phenyl, and naphthyl. Preferred examples of substituents on these groups include halogen atoms such as chlorine and fluorine, C$_{1-4}$ alkyl groups such as tert-butyl, alkoxy groups such as methoxy, an amino group, C$_{1-4}$ alkyl-substituted amino groups such as dimethylamino, and a hydroxyl group.

In the complex of the present invention, the metal atom M is bonded to the other atoms by the coordinate bond.

The preferred complex is a compound represented by the general formula (I'):

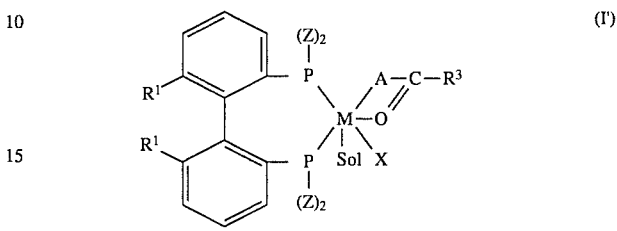

wherein R$^1$, Z, M, A, Sol, X, and R$^3$ have the same meaning as in the general formula (I).

The more preferred complex is a compound represented by the general formula (I''):

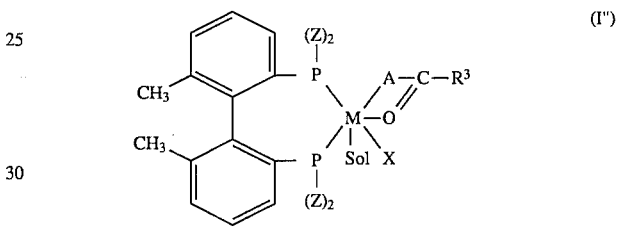

wherein Z, M, A, Sol, X and R$^3$ have the same meaning as in the general formula (I).

The transition metal complex of the present invention can be prepared by a method which comprises reacting a transition metal complex represented by the following general formula (II):

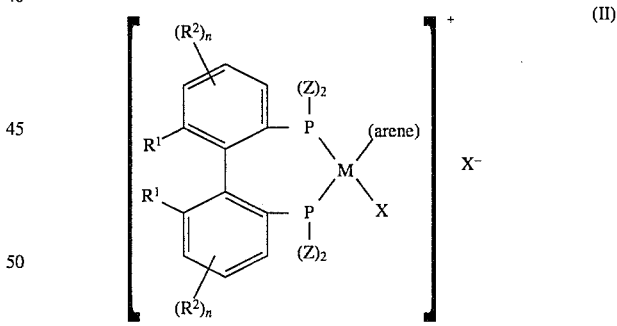

wherein R$^1$, R$^2$, n, Z, X and M are as defined above, and (arene) represents benzene or a substituted benzene having one or more substituents selected from C$_{1-4}$ straight-chain or branched alkyl groups, with a compound represented by the general formula (III) in a solvent:

wherein A and R$^3$ are as defined above.

In the general formula (II), (arene) is preferably a substituted benzene having an alkyl group such as methyl, ethyl and isopropyl as a substituent. The (arene) is bonded to the "M" by the coordinate bond.

The preferred transition metal complex is a compound represented by the general formula (II'):

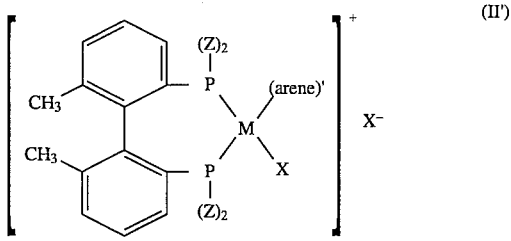

wherein Z, X and M have the same meaning as in the general formula (II), and (arene)' is p-cymene.

The preparation of the compound represented by the general formula (II) can be accomplished by any known method as disclosed in *Tetrahedron Lett.*, vol. 34, pp. 2351–2354 (1993).

Referring to an example of the process for the preparation of the foregoing complex, a ruthenium compound represented by the general formula $[RuX_2(Ar)]_2$ (wherein X represents I or Cl, and Ar represents p-cymene) is reacted with BICHEP. The BICHEP-Ru complex thus prepared is then reacted with a compound represented by the general formula (III) to prepare a complex of the present invention.

In the general formula (III), $R^5$, $R^6$ and $R^7$ each is preferably a hydrogen atom, or a $C_{1-7}$ alkyl group such as methyl, ethyl and heptyl, a $C_{3-6}$ alkenyl group such as heptenyl, a phenyl group or a naphthyl group which may be substituted with a hydroxyl group, an alkoxy group, an amino group, a $C_{1-3}$ alkyl-substituted amino group, a chlorine atom, a bromine atom, etc. In the general formula (III), A is as defined above. The compound represented by the general formula (III) is preferably an unsaturated acid or a ketone.

Preferred examples of the unsaturated acid include tiglic acid, angelic acid, geranic acid, 2-pentenoic acid, 2-methylenephenylacetic acid, 5-methylenenonanoic acid, 2-(6-methoxy naphthalene)propenoic acid, 3-methylcinnamic acid, 6-phenylcinnamic acid, 2-phenyl-2-propenoic acid, 2-(4-methoxyphenyl)- 2-propenoic acid,. 2-(4-hydroxyphenyl)-2-propenoic acid, 2-(4-chlorophenyl)-2-propenoic acid, 2-(4-bromophenyl)- 2-propenoic acid, 2-(4-aminophenyl)-2-propenoic acid, 2-(4-N,N-dimethylaminophenyl)-2-propenoic acid, 2-(4-isobutylphenyl)- 2-propenoic acid, and 3-methyl-2,5-hexadienoic acid.

Preferred examples of the ketone include N-ethylphenylglyoxylamide, N-butylphenylglyoxylamide, N-t-butylphenylglyoxylamide, N-phenylphenylglyoxylamide, N-benzylphenylglyoxylamide, N-phenylpropylglyoxylamide, N-benzylbutylglyoxylamide, methyl pyruvate, methyl phenylglyoxylate, and methyl 2-oxo-4-phenylbutanate.

A preferred process for the preparation of the transition metal complex represented by the general formula (I) of the present invention will be described hereinafter.

To 1 mol of a complex represented by the general formula (II) are added 1 to 5 mols, preferably 1 to 3 mols, more preferably 1 to 1.2 mols of a compound represented by the general formula (III).

The mixture is then allowed to undergo reaction at a temperature of 5° to 60° C. for 0.1 to 20 hours, preferably at a temperature of 10° to 40° C. for 0.5 to 10 hours, more preferably at a temperature of 10° to 30° C. for 1 to 8 hours.

The order of addition of the foregoing complex, compound represented by the general formula (III), solvent, etc., may be arbitrarily altered as far as the predetermined objects are accomplished.

The transition metal complex of the general formula (I) thus obtained is particularly useful as a catalyst for the asymmetric hydrogenation reaction of an unsaturated acid or a ketone.

Examples of the ketone include glyoxylamide derivatives, ketonic acids and ester derivatives thereof. Specifically, those previously described are preferred. Examples of the ketone other than those previously described include phenylglyoxylic acids. In particular, N-t-butylphenylglyoxylamide is preferred.

As the unsaturated acid there may be preferably used an α- or β- unsaturated acid. Specific examples of such an α- or β- unsaturated acid include unsaturated monocarboxylic acids such as tiglic acid, angelic acid, 3-phenyl-2-butenic acid, atropic acid, 2,3-dimethyl-2-butenic acid and 2-(6-methoxy- 2-naphthyl)-acrylic acid, and unsaturated dicarboxylic acids such as itaconic acid, 2-methyl-maleic acid, 2-methyl-fumaric acid and benzylsuccinic acid. Particularly preferred among these unsaturated acids is tiglic acid.

The reaction condition of the asymmetric hydrogenation will be described hereinafter.

The foregoing unsaturated acid or ketone and the complex represented by the general formula (I) are heated with stirring in a solvent in an atmosphere of hydrogen to effect the asymmetric hydrogenation of the unsaturated acid or ketone. The solvent may have a base incorporated therein. Specific examples of the base preferably include trialkylamines such as triethylamine, triisopropylamine and tributylamine, dialkylamines such as diisopropylamine, and alkali metal salts such as sodium hydroxide, sodium carbonate, sodium bicarbonate, potassium hydroxide, potassium carbonate, and potassium bicarbonate.

The reaction condition of the asymmetric hydrogenation will be further described hereinafter.

When the mixing ratio of the unsaturated acid or ketone to the complex is 100 to 10,000 mols based on 1 mol of the complex, favorable results can be attained. The asymmetric hydrogenation reaction is preferably effected at a temperature of from −20° to 50° C., particularly from 20° to 40° C. As the solvent for use in the hydrogenation reaction there may be used those previously described, particularly methanol. As the base to be incorporated in the solvent there may be used those previously described, particularly triethylamine and sodium carbonate.

The amount of the base to be incorporated is in the range of 1 to 200 gram atoms based on 1 gram atom of the transition metal. The amount of the solvent to be used is in the range of 1 to 10 mols based on 1 mol of the unsaturated acid or ketone.

In the asymmetric hydrogenation reaction, the R-isomer or S-isomer of phosphine in the complex represented by the general formula (I) can be selected to provide a free preparation of an asymmetrically hydrogenated compound in the form of the R-isomer or S-isomer. In this manner, the optical purity of the product can be easily controlled to not less than 90%, particularly not less than 95%.

When the complex represented by the general formula (I) is allowed to stand in an atmosphere of hydrogen gas, the moiety derived from the compound of the general formula (III) present in the complex is asymmetrically hydrogenated to give an asymmetrically hydrogenated compound of the complex of the general formula (I). The asymmetric hydrogenation is preferably effected at a temperature of 10° to 30° C. under a pressure of 1 to 10 atm. (hydrogen partial pressure) for 1 minute to 1 hour.

The present invention will be further described in the following examples, but the present invention should not be construed as being limited thereto. The figures as used hereinafter are by weight unless otherwise specified.

EXAMPLE 1

(Preparation of [RuI((R)-BICHEP)(p-cymene)]I complex)

269 mg (0.274 mmol) of [RuI$_2$(p-cymene)]$_2$ and 316 mg (0.549 mmol) of (R)-BICHEP were dissolved in 20 ml of methanol. To the solution was then added 10 ml of dichloromethane. The reaction mixture was then heated under reflux for 4 hours to undergo reaction. The solvent was then distilled off from the reaction mixture under reduced pressure. The residue was then washed with 10 ml of diethyl ether five times. The product was then recrystallized from a solvent mixture of 8 ml of dichloromethane and 2 ml of diethyl ether to prepare [RuI((R)-BICHEP)(p-cymene)]I complex.

(Preparation of complex of [RuI((R)-BICHEP)(p-cymene)]I complex with N-t-butylphenylglyoxyamide)

76.0 mg (0.1 mmol) of [RuI((R)-BICHEP)(p-cymene)] and 61.6 mg (0.3 mmol) of N-t-butylphenylglyoxyamide were added to 2 ml of dichloromethane. The mixture was then stirred at room temperature in an atmosphere of nitrogen gas for 1 hour.

The resulting brown dispersion was then solidified with liquid nitrogen. The solidified material was then degassed in vacuo three times. As a result, a purple solution was obtained. The solvent was then removed from the solution. The residue was then recrystallized from a mixture of 2 ml of methanol and 5 ml of diethyl ether to obtain 35 mg (0.03 mmol) of a bluish violet solid (yield: 32%).

The compound thus obtained exhibited the following NMR and IR values:

$^1$H-NMR (400 MHz, CD$_2$Cl$_2$); δ-0.37–2.30 (m, 44H), 0.92 (s, 9H), 2.04, 2.10 (s, 3H), 6.28 (br, NH, (H)), 7.28–7.55 (m, ArH, 11H), $^{31}$P-NMR (162 MHz, CD$_2$Cl$_2$); δ, 24.8 ppm (d, J=37 Hz), 26.8 ppm (d, J=36 Hz), 82.2 ppm (d, J=36 Hz), 85.7 ppm (d, J=37 Hz), IR (KBr) (νCOO), 1658, 1648 cm$^{-1}$

EXAMPLE 2

(Preparation of complex of [RuI((R)-BICHEP)(p-cymene)]I complex with tiglic acid)

117.5 mg (0.110 mmol) of [RuI((R)-BICHEP)(p-cymene)]I complex obtained in Example 1 and 15.2 mg (0.11 mmol) of potassium tiglate were added to 1 ml of chloroform. The mixture was then stirred at room temperature for 5 hours. The mixture was then filtered through a Celite 545 pad. The residue was then washed with 3 ml of chloroform. The filtrate was then evaporated to dryness to obtain 90 mg (0.088 mmol) of a brown reaction product (yield: 80%).

The compound thus obtained exhibited the following NMR and IR values:

$^1$H-NMR (400 MHz, CDCl$_3$); δ-0.40–3.40 (m, C$_6$H$_{11}$, CH$_3$, 56H), 6.20 (br., =CH—, 1H), 6.65–7.55 (m, aromatic, 6H), $^{31}$P-NMR (162 MHz, CDCl$_3$); δ, 24.0, 85.4, (d, Jp-p=39 Hz), IR (KBr) (νCOO), 1438 cm$^{-1}$ (νC=C)

APPLICATION EXAMPLE 1

(Hydrogenation of Complex)

10.9 mg (1×10$^{-2}$ mol) of the complex obtained in Example 1 were added to 2 ml of methanol. The mixture was then hydrogenated at room temperature in an atmosphere of hydrogen gas under a pressure of 5 atm.

After 30 minutes, a complex was obtained in the form of S-isomer (optical purity: 98%).

APPLICATION EXAMPLE 2

(Hydrogenation of Complex)

3.3 mg (3.1×10$^{-3}$ mol) of the complex obtained in Example 2 were added to 2 ml of methanol (containing 44.0 mg (0.53 mmol) of Na$_2$CO$_3$). The mixture was then hydrogenated at a temperature of 25° C. in an atmosphere of hydrogen gas under a pressure of 5 atm. for 10 minutes. As a result, a complex was obtained in the form of S-isomer (optical purity: 95%).

EXAMPLE 3

(Hydrogenation of N-t-butylphenylglyoxyamide)

5.5 mg (5×10$^{-3}$ mol) of the complex obtained in Example 1 and 2 ml of methanol were charged into a 50-ml vessel equipped with a magnetic stirrer. To the mixture were then added 205 mg (1 mmol) of N-t-butylphenylglyoxyamide. The reaction mixture was then hydrogenated at room temperature under a pressure of 3 atm. in an atmosphere of hydrogen gas.

After 1 hour, a complex was obtained in the form of S-isomer (optical purity: 98%).

EXAMPLE 4

(Hydrogenation of Tiglic Acid)

5.9 mg (5.5×10$^{-2}$ mol) of the complex obtained in Example 2 were added to 20 ml of methylene chloride. To the mixture were then added 1.33 g (13.3 mmol) of tiglic acid. The mixture was then hydrogenated at room temperature under a hydrogen pressure of 5 atm for 2 hours. As a result, an asymmetrically hydrogenated compound of tiglic acid was obtained in the form of S-isomer (optical purity: 91%).

The asymmetrically hydrogenated compound thus obtained exhibited a rotation angle ($[α]_D^{25}$) of +17.93 (neat) and the following NMR values:

$^1$H-NMR (400 MHz, CDCl$_3$); δ-0.94 (brd, 2.95H, J=7.3 Hz, CH$_3$), 1.17 (d, 3.01H, J=6.9 Hz, 3H), 1.15–2.00 (m, 2H), 2.40 (m, 1H), 9.76 (S, 1H)

In accordance with the present invention, a novel asymmetric hydrogenation catalyst can be provided. The use of such a catalyst can provide an easy and efficient preparation of an optically active carboxylic acid with a high optical purity as an asymmetrically hydrogenated unsaturated aliphatic acid.

While the invention has been described in detail and with reference to specific embodiments thereof, it will be apparent to one skilled in the art that various changes and modifications can be made therein without departing from the spirit and scope thereof.

What is claimed is:

1. A transition metal complex represented by the general formula (I):

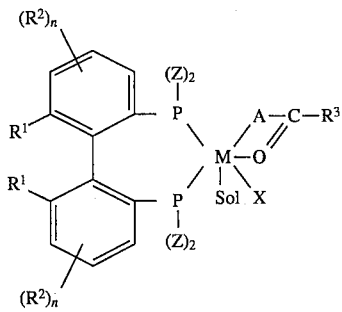

wherein $R^1$ and $R^2$ each represents a halogen atom, a $C_{1-3}$ alkyl group, or a $C_{1-3}$ alkyl group substituted with a halogen atom; n represents 0 or an integer of from 1 to 3; Z represents a cyclohexyl group, a phenyl group, or a substituted phenyl group, wherein said substituted group is a $C_{1-4}$ alkyl group, a $C_{1-4}$ alkoxy group or a halogen atom; X represents a chlorine atom, a bromine atom, or an iodine atom; M represents a ruthenium atom, a rhodium atom, an iridium atom, a palladium atom, or a platinum atom; Sol represents a solvent; A represents —O— or —O=C($R^4$)—; $R^4$ is selected from the group consisting of

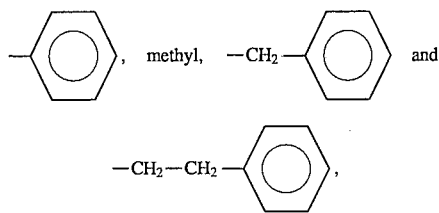

wherein the phenyl nucleus may be substituted with a $C_{1-4}$ alkyl group; and when A is —O—, $R^3$ represents —C($R^7$)=C($R^5$)$R^6$ and when A is —O=C($R^4$)—, $R^3$ represents —NH-tert-butyl,

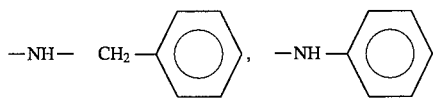

or —OCH$_3$, wherein $R^5$, $R^6$ and $R^7$ each represents a hydrogen atom, a $C_{1-7}$ alkyl or alkenyl group which may be substituted, or a $C_{6-18}$ aryl or naphthyl group which may be substituted, with the proviso that $R^5$, $R^6$ and $R^7$ are not hydrogen atoms at the same time, that when $R^5$ and $R^6$ are hydrogen atoms at the same time, $R^7$ is not a methyl group, and that when $R^7$ is a hydrogen atom, $R^5$ and $R^6$ are different groups other than a hydrogen atom.

2. The complex according to claim 1, wherein said compound represented by the general formula (I) is a complex represented by the general formula (I'):

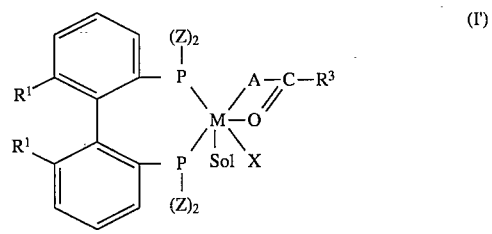

wherein $R^1$, Z, M, A, Sol, X and $R^3$ have the same meaning as in the general formula (I).

3. The complex according to claim 1, wherein said compound represented by the general formula (I) is a complex represented by the general formula (I''):

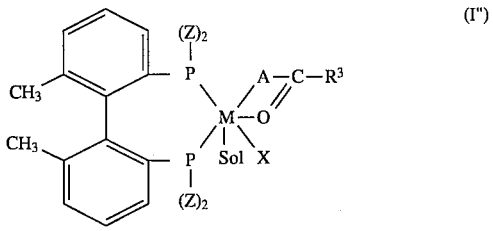

wherein Z, M, A, Sol, X and $R^3$ have the same meaning as in the general formula (I).

4. The complex according to claim 1 or 2, wherein A is —O—.

5. The complex according to claim 1 or 2, wherein A is —O=C($R^4$)—.

6. The complex according to claim 1 or 2, wherein M is a ruthenium atom or a rhodium atom.

7. The complex according to claim 1 or 2, wherein Z is a cyclohexyl group.

8. The complex according to claim 4, wherein M is a ruthenium atom and Z is a cyclohexyl group.

9. The complex according to claim 5, wherein M is a rhodium atom and Z is a cyclohexyl group.

10. A process for the preparation of a transition metal complex represented by the general formula (I):

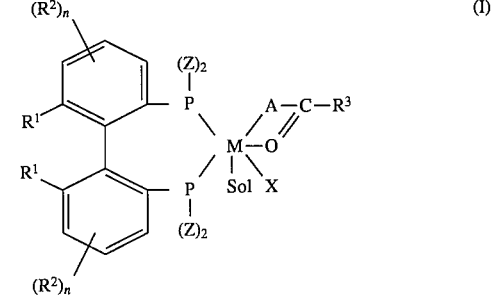

wherein $R^1$ and $R^2$ each represents a halogen atom, a $C_{1-3}$ alkyl group, or a $C_{1-3}$ alkyl group substituted with a halogen atom; n represents 0 or an integer of from 1 to 3; Z represents a cyclohexyl group, a phenyl group, or a substituted phenyl group, wherein said substituted group is a $C_{1-4}$ alkyl group, a $C_{1-4}$ alkoxy group or a halogen atom; X represents a chlorine atom, a bromine atom, or an iodine atom; M represents a ruthenium atom, a rhodium atom, an iridium atom, a palladium atom, or a platinum atom; Sol represents a solvent; A represents —O— or —O=C($R^4$)—; $R^4$ is selected from the group consisting of

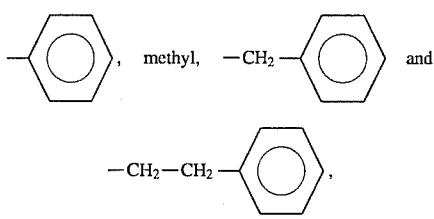

wherein the phenyl nucleus may be substituted with a $C_{1-4}$ alkyl group; and when A is —O—, $R^3$ represents —C($R^7$)═C($R^5$)$R^6$ and when A is —O═C($R^4$)—, $R^3$ represents —NH-tert-butyl,

or —OCH$_3$, wherein $R^5$, $R^6$ and $R^7$ each represents a hydrogen atom, a $C_{1-7}$ alkyl or alkenyl group which may be substituted, or a $C_{6-18}$ aryl or naphthyl group which may be substituted, with the proviso that $R^5$, $R^6$ and $R^7$ are not hydrogen atoms at the same time, that when $R^5$ and $R^6$ are hydrogen atoms at the same time, $R^7$ is not a methyl group, and that when $R^7$ is a hydrogen atom, $R^5$ and $R^6$ are different groups other than a hydrogen atom, which comprises reacting a transition metal complex represented by the general formula (II):

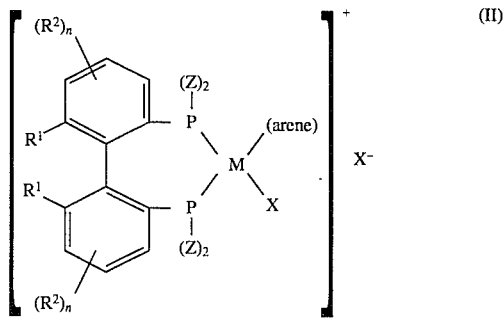

wherein $R^1$, $R^2$, n, Z, X and M are as defined above, and (arene) represents benzene or a substituted benzene having one or more substituents selected from $C_{1-4}$ straight-chain or branched alkyl groups, with a compound represented by the general formula (III) in a solvent:

wherein A and $R^3$ are as defined above.

11. The process for the preparation of a complex according to claim 10, wherein said compound represented by the general formula (II) is a complex represented by the general formula (II'):

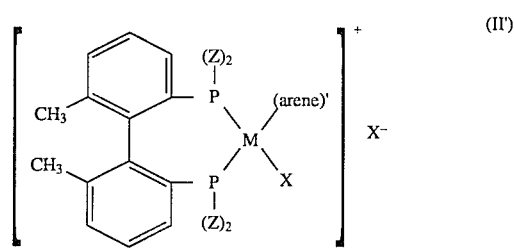

wherein Z, X and M have the same meaning as in the general formula (II), and (arene)' is p-cymene.

12. An asymmetric hydrogenation catalyst comprising a transition metal complex represented by the general formula (I):

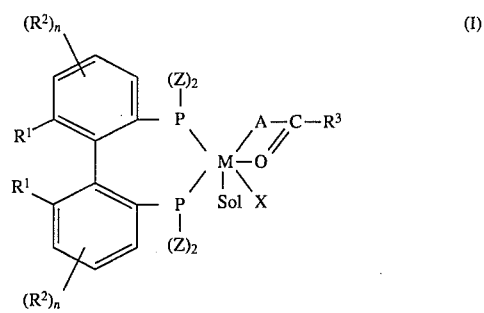

wherein $R^1$ and $R^2$ each represents a halogen atom, a $C_{1-3}$ alkyl group, or a $C_{1-3}$ alkyl group substituted with a halogen atom; n represents 0 or an integer of from 1 to 3; Z represents a cyclohexyl group, a phenyl group, or a substituted phenyl group, wherein said substituted group is a $C_{1-4}$ alkyl group, a $C_{1-4}$ alkoxy group or a halogen atom; X represents a chlorine atom, a bromine atom, or an iodine atom; M represents a ruthenium atom, a rhodium atom, an iridium atom, a palladium atom, or a platinum atom; Sol represents a solvent; A represents —O— or —O═C($R^4$)—; $R^4$ is selected from the group consisting of

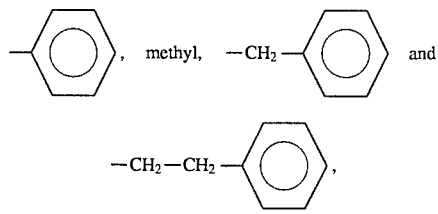

wherein the phenyl nucleus may be substituted with a $C_{1-4}$ alkyl group; and when A is —O—, $R^3$ represents —C($R^7$)═C($R^5$)$R^6$ and when A is —O═C($R^4$)—, $R^3$ represents —NH-tert-butyl,

or —OCH$_3$, wherein $R^5$, $R^6$ and $R^7$ each represents a hydrogen atom, a $C_{1-7}$ alkyl or alkenyl group which may be substituted, or a $C_{6-18}$ aryl or naphthyl group which may be substituted, with the proviso that $R^5$, $R^6$ and $R^7$ are not hydrogen atoms at the same time, that when $R^5$ and $R^6$ are hydrogen atoms at the same time, $R^7$ is not a methyl group, and that when $R^7$ is a hydrogen atom, $R^5$ and $R^6$ are different groups other than a hydrogen atom.

13. The asymmetric hydrogenation catalyst according to claim 12, wherein said compound represented by the general formula (I) is a complex represented by the general formula (I'):

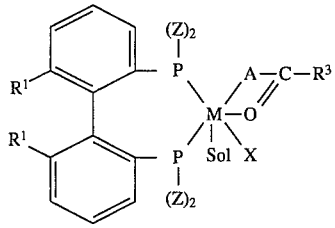

(I')

wherein $R^1$, Z, M, A, Sol, X and $R^3$ have the same meaning as in the general formula (I).

14. The asymmetric hydrogenation catalyst according to claim 12, wherein said compound represented by the general formula (I) is a complex represented by the general formula (I"):

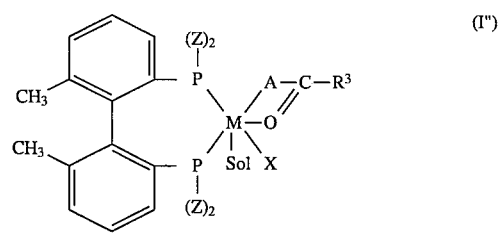

(I")

wherein Z, M, A, Sol, X and $R^3$ have the same meaning as in the general formula (I).

15. The asymmetric hydrogenation catalyst according to claim 12, wherein A is —O—.

16. The asymmetric hydrogenation catalyst according to claim 12, wherein A is —O=C($R^4$)—.

17. The asymmetric hydrogenation catalyst according to claim 12, wherein M is a ruthenium atom or a rhodium atom.

18. The asymmetric hydrogenation catalyst according to claim 12, wherein Z is a cyclohexyl group.

19. The asymmetric hydrogenation catalyst according to claim 15, wherein M is a ruthenium atom and Z is a cyclohexyl group.

20. The asymmetric hydrogenation catalyst according to claim 16, wherein M is a ruthenium atom and Z is a cyclohexyl group.

\* \* \* \* \*